United States Patent [19]

Kerr, deceased et al.

[11] Patent Number: 4,534,340

[45] Date of Patent: Aug. 13, 1985

[54] COMBINATION HANDLE

[75] Inventors: Ronald R. Kerr, deceased, late of Fort Collins, Colo., by Blanche S. Kerr, executrix; David W. Smith; John M. Trenary, both of Fort Collins, Colo.

[73] Assignee: Teledyne Industries, Inc., Fort Collins, Colo.

[21] Appl. No.: 519,145

[22] Filed: Aug. 1, 1983

[51] Int. Cl.³ .............................................. A46B 13/06
[52] U.S. Cl. ...................................... 128/66; 15/22 R
[58] Field of Search ................. 128/66, 62 A; 433/80; D24/10, 11, 15; 132/284; 15/22 R

[56] References Cited

U.S. PATENT DOCUMENTS

| | | |
|---|---|---|
| Re. 27,274 | 1/1972 | Mattingly . |
| 3,227,158 | 1/1966 | Mattingly ............................... 128/66 |
| 3,273,189 | 9/1966 | Levinson et al. ...................... 128/66 |
| 3,425,410 | 2/1969 | Cammack ............................... 128/66 |
| 3,453,969 | 7/1969 | Mattingly ............................. 417/448 |
| 3,467,083 | 9/1969 | Mattingly ............................... 128/66 |
| 3,484,885 | 12/1969 | Deines et al. ....................... 15/22 R |
| 3,509,874 | 5/1970 | Stillman ................................. 128/66 |
| 3,524,208 | 8/1970 | Mattingly ............................ 15/22 R |
| 3,551,931 | 1/1971 | Monroe et al. ........................ 128/15 |
| 3,561,033 | 2/1971 | Trenary et al. ...................... 15/22 R |
| 3,771,186 | 11/1973 | Moret et al. ........................... 128/66 |
| 3,966,359 | 6/1976 | Woog ..................................... 128/66 |
| 4,108,167 | 8/1978 | Hickman et al. ...................... 128/66 |
| 4,146,020 | 3/1979 | Moret et al. ....................... 128/62 A |
| 4,302,186 | 11/1981 | Cammack et al. ..................... 433/80 |
| 4,365,376 | 12/1982 | Oda et al. .......................... 128/62 A |
| 4,442,831 | 4/1984 | Trenary ................................. 128/66 |

Primary Examiner—Richard J. Johnson
Attorney, Agent, or Firm—Hugh H. Drake

[57] ABSTRACT

Successively-delivered liquid pulses are led into an elongated hollowed handle of a size and shape to be grasped by the human hand. A nozzle, mounted to the handle, delivers those pulses against the teeth and gums of the user. Also mounted to the handle is a toothbrush for scrubbing the teeth and massaging the gums. Included within the handle are elements that cooperate to drive the toothbrush relative thereto.

2 Claims, 6 Drawing Figures

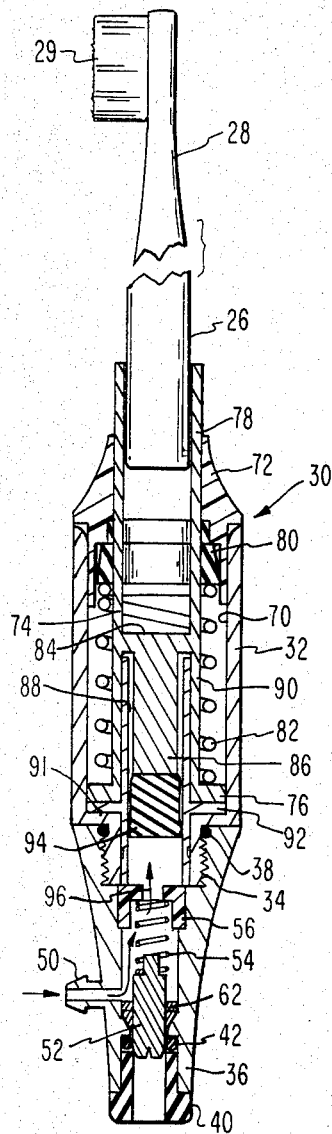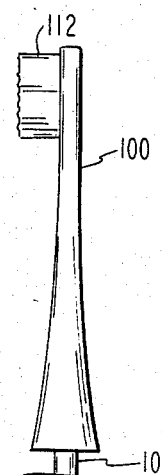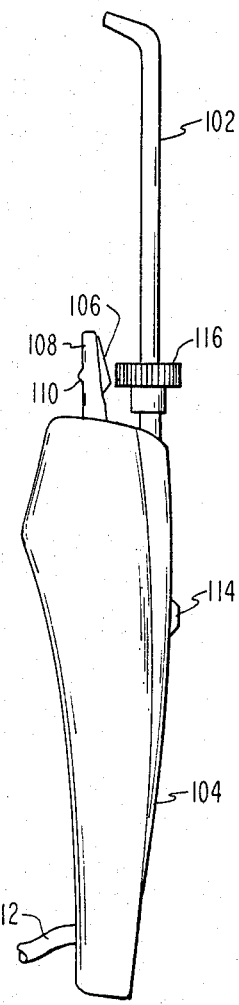
FIG. 3
FIG. 4
FIG. 5

COMBINATION HANDLE

The present invention pertains to oral hygiene apparatus. More particularly, it relates to a combination in such apparatus which provides both toothbrushing and oral irrigation.

Beginning at least as early as the disclosure in U.S. Pat. No. 3,393,673-Mattingly, numerous devices have been disclosed and marketed for irrigating a person's mouth in order to cleanse the teeth and massage the gums. Typical of other and related apparatus for that purpose are the disclosures in U.S. Pat. Nos. 3,227,158, RE. 27,274, 2,453,969, 3,467,083, 3,425,410, 4,108,167 and 4,302,186. Both the common general approach of all of those patents and the detailed approaches of different ones of them have found significant user acceptance.

All of the aforementioned apparatus involve a unit for producing a succession of water pulses. Such a unit typically includes a piston-type pump which accepts water from a source, such as a reservoir, and delivers it through hosing to a nozzle. The nozzle is manipulated by the user for the purpose of achieving the ultimate gum massage and teeth cleaning.

In addition to irrigation, many users desire, and dentists may recommend, additional scrubbing and/or massaging by use of a brush. Of course, that may be accomplished by means of a hand-held manually-manipulated toothbrush. Nevertheless, electrically-powered toothbrushes came into existence. Some use electro-mechanical vibrators, while others use electric motors. Also created have been air-driven toothbrushing apparatus perhaps more usually for use by a dentist.

In the evolution of the art, a related but yet different approach was revealed in U.S. Pat. Nos. 3,484,885-Deines et al, 3,524,208-Mattingly, 3,551,931-Monroe et al, and 3,561,033-Trenary et al. In the subject matter of the latter patents, advantage was taken of the existence of the successive water pulses in oral irrigating apparatus to power an hydraulic motor in a toothbrush unit. Variations among the different specific approaches provided for a driving of the toothbrush in any one or more of reciprocating, rotary or elliptical motion patterns. To employ that approach, the user has had to select either the toothbrush unit or the oral irrigation nozzle unit, selectively attaching one or the other to the water pumping apparatus. That has meant a necessity to turn off the pumping apparatus in order to change between one mode of application and the other. It also has required an uneconomical redundancy of common components such as in the different handles to be grasped by the user during use of either the nozzle or the brush.

It is, accordingly, a general object of the present invention to provide a new and improved oral hygiene apparatus which achieves at least many of the same aims as in all of the foregoing apparatus but yet accomplishes the task in a manner which overcomes deficiencies in the prior approaches.

Another object of the present invention is to provide a new and improved oral hygiene apparatus which retains the advantage of the foregoing and yet which accomplishes the same in a more economical manner.

A further object of the present invention is to provide a new and improved oral hygiene apparatus which incorporates both brushing and irrigation modes, while tending to minimize redundancy of components employed.

Oral hygiene apparatus constructed in accordance with the present invention includes a source of a succession of liquid pulses. An elongated, hollow handle of a size and shape to be grasped by the human hand is coupled to means for delivering those pulses into the interior of the handle. A nozzle delivers the pulses against the teeth and gums of the user, and there are means for mounting that nozzle in the handle for receiving those pulses. A toothbrush, for scrubbing the teeth and massaging the gums, also is mounted to the handle. Included within the handle are means for moving the toothbrush relative to the handle.

The features of the present invention which are believed to be patentable are set forth with particularity in the appended claims. The organization and manner of operation of the invention, together with further objects and advantages thereof, may best be understood by reference to the following description taken in connection with the accompanying drawings, in the several figures of which like reference numerals identify like elements, and in which:

FIG. 3 is a similar view of the version of FIG. 2 with a toothbrush mounted in a use position;

FIG. 4 is a side elevational view of a modified version of the handle of FIG. 1 with a toothbrush mounted for use;

FIG. 5 is a view similar to FIG. 4 but with a nozzle mounted for use; and

A pumping unit 10 feeds slugs or successive pulses of water or other liquid through a hose 12. Unit 10 preferably includes a piston-type pump for most conveniently producing the water pulses. The particular version of pumping unit 10 illustrated is that shown and described in U.S. Pat. No. Re. 27,274. However, the pumping unit of any of the other oral irrigation patents also mentioned in the introduction may instead be employed.

Whichever pumping unit is selected, there must be sufficient pressure developed inherently or by selection to drive the embodied apparatus. As will be observed, pressure variation may affect volume or degree of action. Whichever of the pumping units of the prior apparatus might be selected for use in the herein disclosed new combination, those prior disclosures are incorporated herein by reference, so as to enable choice of a suitable pumping unit.

Figures 1, 2:
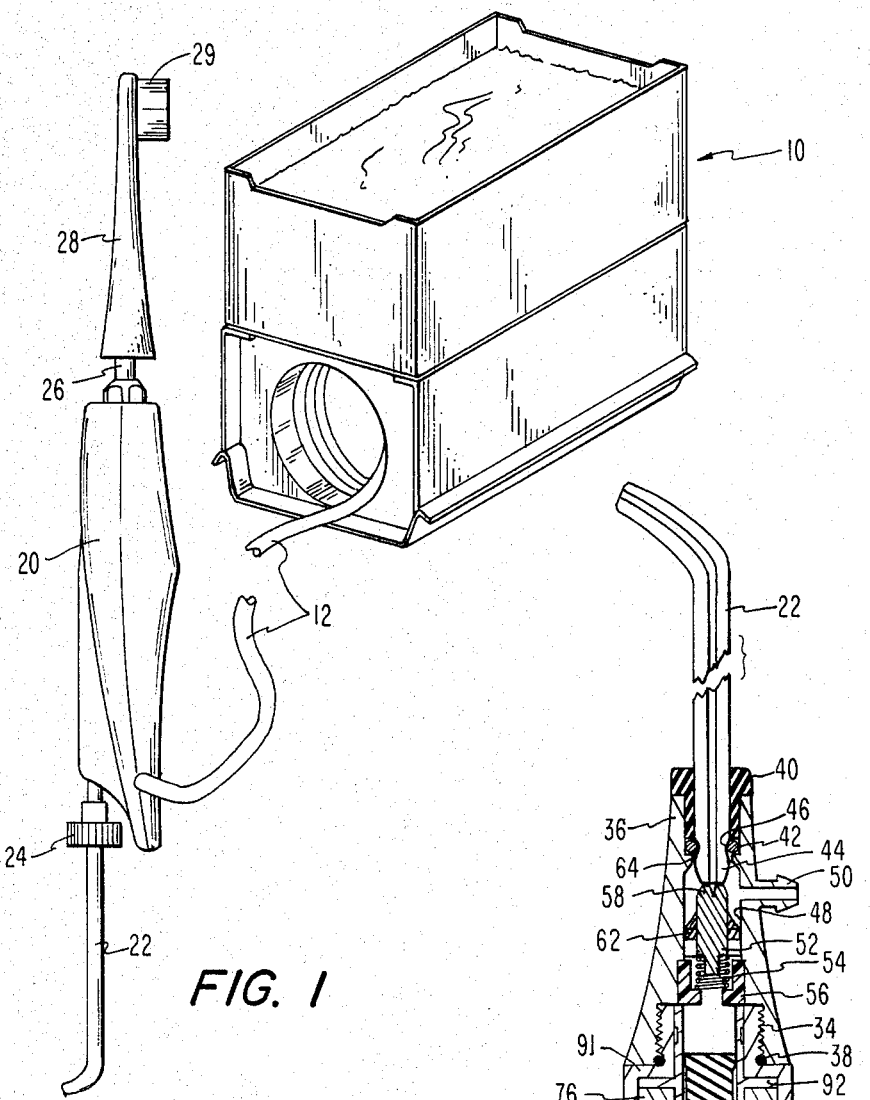
FIG. 1 is an isometric view of a source of water pulses coupled to a combination oral hygiene handle.
FIG. 2 is a longitudinal cross-sectional view of one specific handle version with a nozzle mounted in use position.

Hose 12 leads from pumping unit 10 into a handle 20 as shown in FIG. 1. Handle 20 is elongated in shape and sized so as to be conveniently grasped by the human hand. Projecting from one end of handle 20 is a nozzle 22 on the protruding portion of which is a manipulating knob 24. Projecting from the opposing end of handle 20 is a drive shaft 26 on the outer end of which is seated a toothbrush 28 that has conventional bristles 29.

In the less stylized version of FIGS. 2 and 3, a handle 30, includes a hollow, cylindrical housing 32 onto one end of which is mounted, as by threads 34, a nose cone 36 sealed in place by an 0-ring 38. Pressed into the outer end of cone 36 is a retainer 40 which captivates an 0-ring 42 within the inner bore of cone 36. Nozzle 22 includes, on its insertable end portion 44, an annular groove 46 located to seat on O-ring 42 when nozzle 22 is in place.

Also defined within cone 36 is an interior chamber 48 into which communicates a nipple 50 onto which hose 12 is connected for the delivery of water pulses from pumping unit 10. Free-floating within cavity 48 is a valve 52 biased toward nozzle 22 by a compression spring 54 held in place within cone 36 by a retainer 56.

In the mode of operation illustrated in FIG. 2, end 44 of nozzle 22 forces valve 52 into an open position relative to the path to nipple 50. The upper end of valve 52 is formed as a spider having circumferentially-displaced inlets 58, so that, in this mode of operation, water pulses inletted through nipple 50 flow through those openings and on into nozzle 22 to be delivered into the mouth of the user. Accordingly, that mode of operation is in accordance with what would be the normal irrigation mode of the use of pumping unit 10.

When, however, nozzle 22 is removed from handle 20, spring 54 forces valve 52 into sealing engagement within O-ring 42 as shown in FIG. 3. Thereupon, inletted water pulses cannot flow outwardly along the path toward where the nozzle was inserted. An exteriorly-projecting guide ring 62 formed annularly around the body of valve 52 insures positive seating of valve 52 in sealing relationship within O-ring 42 by reason of the incoming pressure of the water pulses. It will be noted that ring 62 seats upwardly against a lug formation which also serves as part of the captivation of O-ring 42.

Housing 32 defines an inner bore 70, closed at the brush end by an end housing or retainer 72. Slidably movable longitudinally within bore 70 is an elongated tube 74 that has an annulus 76 around its inner end which rides snugly within bore 70. The other end portion 78 of tube 74 slides within end retainer 72. A spacer 80 for tube 74 also is captivated within bore 70 by retainer 72. Closely encircling tube 72 within bore 70 is a compression spring 82. Spring 82 is compressed between spacer 80 and annulus 76, the spring being preloaded during assembly by the spacer.

Intermediate the length and interiorly of tube 74 is a cross wall 84 from which inwardly projects a rod 86. Rod 86 has a diameter sufficiently smaller than the internal diameter of tube 74 so as to define an annular channel 88 within which projects a cylinder 90. The opposite end portion of cylinder 90 continues into the region of housing 32 which carries threads 34 and is heat staked or otherwise secured thereto. At the end of bore 70 nearest nose cone 36 is a circumferential shoulder 91 adjacent to a flange 92 projecting outwardly from cylinder 90 and on which annulus 76 seats under the action of spring 82.

Snugly riding within cylinder 90 is a piston 94. With valve 52 posed in the position of FIG. 2 by virtue of the insertion of nozzle 22, the water pulses not only are flowing outwardly through the nozzle but all components within the main body of housing 32 are stationary. When, however, nozzle 22 has been removed, valve 52 is urged by spring 54 into the position shown in FIG. 3, whereupon water pulses inletted through nipple 50 flow past the lower end portion of valve 52 and through the region within spring 54 into cylinder 90 and impact against piston 94 as indicated by arrow 96.

The strength of spring 82 relative to the force exerted by each individually successive water pulse delivered from pump unit 10 is selected so that each such water pulse causes piston 94 to move tube 74 outwardly through retainer 72. Upon cessation of each water pulse, on the other hand, spring 82 returns tube 74 to its more inward location. Accordingly, the succession of received water pulses causes tube or sleeve 74 to reciprocate longitudinally and that, in turn, longitudinally reciprocates bristles 29 on brush 28.

To that end, end portion 26 of the brush handle is detentingly or otherwise secured within outer portion 78 of tube 74. That detent is by way of any convenient means, such as the corrugation of the aforesaid U.S. Pat. No. 3,484,885, a set screw as shown in the aforesaid U.S. Pat. No. 3,524,208, a conventional bayonet connection, a snap-in detent that sits in a groove or it is held in place frictionally as shown.

In this instance, spacer 80 and bore 70 have smooth and continuous inner walls so as to permit sleeve 74 to reciprocate strictly in a linear manner in the longitudinal direction. In the alternative, however, the inner surface of spacer 80, bore 70 or another ensleeving element, may be formed to define a helical or other twisting guideway into which are seated ears which project outwardly from tube 74 into that guideway. Consequently, the longitudinal reciprocation is converted at least in part into a rotation of tube 74 and hence of brush 28. That principle is, in itself, revealed in the aforesaid U.S. Pat. No. 3,551,931 and 3,561,033. Furthermore, the details of the manner of guiding in either of the latter two patents may be incorporated into the present handle units so as selectively to achieve any of linear reciprocation, strictly rotation, or a combination of the two which produces an elliptical movement pattern of bristles 29. In any event, the frequency of reciprocation will be the same as that of the water pulses being delivered through nipple 50. Moreover, adjustment of the pulse pressure at pump unit 10 or elsewhere may be employed in order to provide a degree of adjustment of the length of each stroke of brush 28.

In the alternative arrangement of FIGS. 4 and 5, both a brush 100 and a nozzle 102 are arranged to be mounted and project away from the same end of an elongated handle 104. Inlet hose 12 connects into any convenient location. On handle 104, in this case, a counter bored interior of brush 100 is shaped to fit over the ramp 106 on a post 108 and includes an internal groove which snaps upon a lug 110 formed on post 108. As before, brush 100 includes laterally projecting bristles 112. Projecting through a side wall of handle 104 is a pushbutton 114. Nozzle 102 includes a fingerhold hold 116.

The shape of handle 14 is not particularly critical, except that it may need to be thicker at its upper end as shown in order to accommodate a set of two different mechanisms placed side by side as compared with the specific arrangement of the earlier embodiments wherein the two primary mechanisms are located respectively in opposite portions of handle 20. Nevertheless, the ultimate shape is selected from the standpoint of pleasing appearance and convenience for being grasped by the user. In any case, it is unnecessary to herein describe in detail any particular manner of constructing the handle itself.

Figure 6:
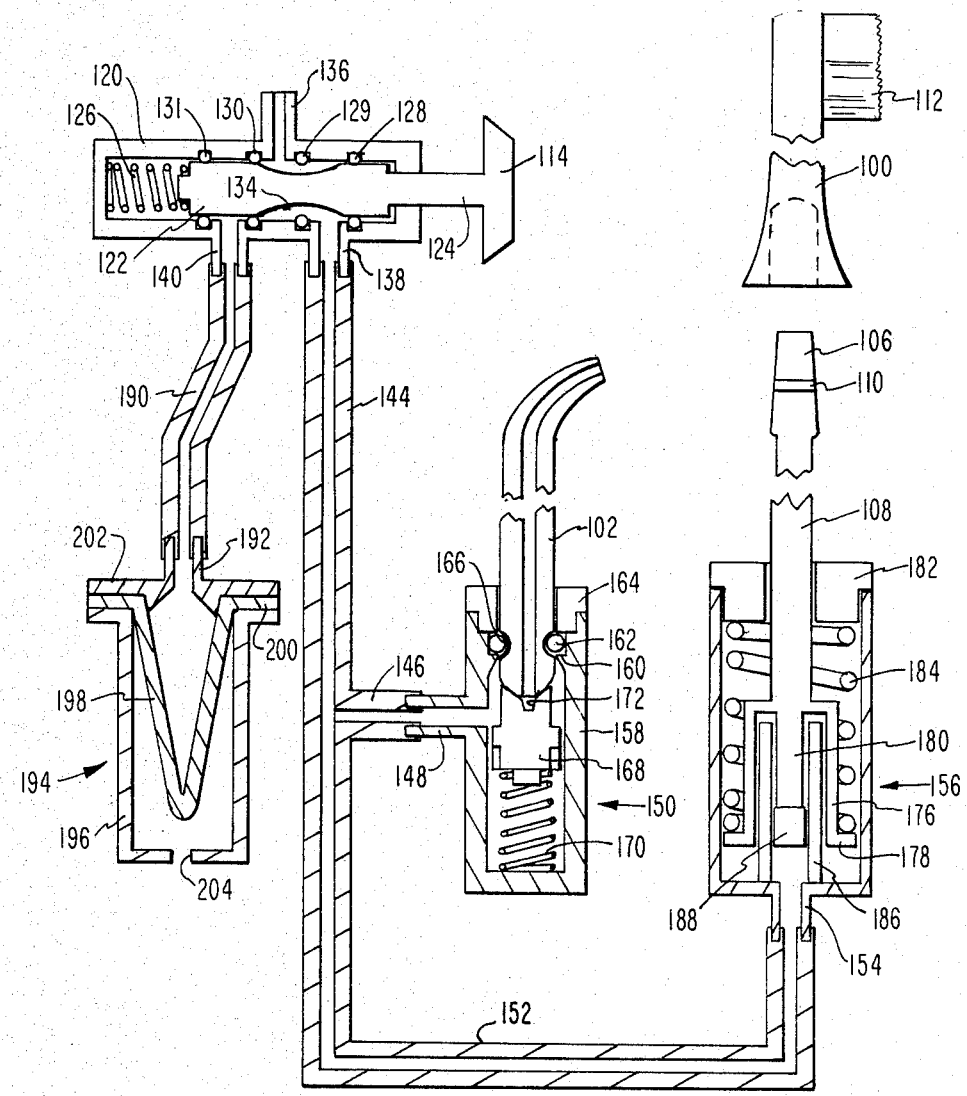
FIG. 6 is an enlarged diagrammatic view of components included in the handle of FIGS. 4 and 5 or in the handle of FIG. 1.

The components desirably to be included within handle 20 or handle 104 are all shown in the diagram of FIG. 6 for convenience of illustration. An elongated hollow valve body 120 supports a valve 122 from one end of which a shank 124 is connected to button 114. Compressed within body 120 is a spring 126 which urges valve 122 into the illustrated position with button 114 protruding outwardly from handle 104. Nested into the interior wall of body 120 and encircling valve 122 are a longitudinally-spaced succession of O-rings 128, 129, 130 and 131. Formed into the wall of valve 122 is a recess 134 which spans a distance slightly less than that between any successive three of O-rings 128-131.

Projecting outwardly from valve body 120 is an inlet nipple 136 and a pair of outlet nipples 138 and 140. Inlet nipple 136 is located so as to allow inletted water pulses from pumping unit 10 to enter the interior of body 120 between O-rings 129 and 130. On the other hand, nipple 138 provides an exit from the interior region between O-rings 128 and 129, while nipple 140 provides an outlet exit from between O-rings 130 and 131. Nipple 138 is connected by a tube 144 from which a first branch 146 is connected to an inlet nipple 148 of an irrigator housing 150, and another branch 152 is connected to the inlet nipple 154 of a toothbrush assembly 156.

With the components of the valve assembly in the position illustrated, incoming water pulses are allowed by recess 134 to flow over O-ring 129 and into tube 144 from which they are conducted both to irrigator housing 150 and toothbrush unit 156. Housing 150 includes a hollow body 158 having a ledge 160 internally projecting to receive an O-ring 162 which is captivated by a retainer 164 through which nozzle 102 is to be inserted. O-ring 162 seats into a corresponding depression 166 formed in the exterior wall of the lower end portion of nozzle 102. Also seated in the interior of body 158 is a valve 168 beneath which is positioned a compression spring 170 which urges valve 168 toward the entrance for nozzle 102.

With nozzle 102 inserted within body 158, the lower end of nozzle 102 urges valve 168 into a downward position in which water pulses inletted through nipple 148 are permitted to traverse openings 172 within the valve and enter into nozzle 102 in essentially the same manner as described with regard to the embodiment of FIG. 2. Also in the manner of the earlier embodiment, when nozzle 102 is removed from unit 150 and from projecting within hollow body 158, valve 168 is forced upwardly so as to seal within O-ring 162 and close the passage for the delivery of water outwardly from hollow body 158.

With the closure of valve 168, all pressure of the incoming water pulses is delivered through branch 152 into nipple 154. Slidably received within the interior of unit 156 is a tube 176 which, again as before, includes a lower flange or annulus 178 and an interior rod 180 from which, in this case, post 108 projects upwardly through a retainer 182. A compression spring 184 seated between flange 178 and retainer 182 urges post 108 toward a lowermost position as illustrated. Secured within unit 156 is an upwardly projecting cylinder 186 within which rides a piston 188 exposed to the force developed by the water pulses inletted through nipple 154.

It will be observed that the operation for reciprocating toothbrush 100 follows the same operational approach as already described in detail with regard to the embodiment of FIG. 3. Until valve 168 in the irrigator has been allowed to move into its closed condition, the pressure of the water pulses beneath piston 188 is insufficient to actuate the toothbrush unit. When, however, valve 168 has moved to its closed condition, those water pulses impacting against piston 188 successively reciprocate post 108, and thus brush 100, back and forth in the longitudinal direction of post 108.

When button 114 is depressed, valve 122 is moved to the left so that recess 134 bridges O-ring 130. In that mode, water pulses inletted through nipple 136 exit from nipple 140 into a tube 190 which leads to a nipple 192 on a pressure accumulator 194. Accumulator 194 includes an elongated hollow body 196 into which projects a resilient bladder 198 captivated around an upper rim 200 by a cover 202 in which nipple 192 is formed. On the lower end of body 196 is a vent 204 which is opened to the atmosphere.

In a typical pumping unit 10, the pressure of the delivered water pulses may be of the order of 160 pounds per square inch. Bladder 198 has a resilience selected to lower the pressure in hose 12 to less than about 80 pounds per square inch. That decreases undesired back loading on pumping unit 10 when button 114 has been pressed into the closed condition as a user may desire to do when changing a brush or moving the nozzle into and out of his mouth. A more detailed description of structure with regard to the incorporation of a resilient bladder in order to achieve such purposes is described and claimed in co-pending U.S. patent application Ser. No. 428,904, filed Sept. 30, 1982, in the name of John M. Trenary. That application is assigned to the same assignee as is the present application.

Whichever embodiment may be employed, there obviously is the advantage of being able to provide in a single handle either oral irrigation apparatus or brushing apparatus all powered hydraulically from a single pumping unit. Accordingly, all of the desired results previously known for either oral irrigation or hydraulically powered toothbrushing are obtained in a more efficient and economical manner. The individually different features of the second embodiment, such as the manual control and accumulator, may be included in the embodiment of FIGS. 2 and 3, and the mechanical approaches of that earlier embodiment may be included in the other. In an alternative, post 108 is modified to have a hollow interior within which nozzle 102 is seated for use in its mode of operation. This amounts to a merger of the different embodiments specifically shown.

While particular embodiments of the invention have been shown and described, and various modifications and alternatives have been taught, it will be obvious to those skilled in the art that changes and modifications may be made without departing from the invention in its broader aspects. Therefore, the aim in the appended claims is to cover all such changes and modifications as fall within the true spirit and scope of that which is patentable It is claimed:
1. Oral hygiene apparatus comprising: a source of a succession of liquid pulses;
   an elongated, hollowed handle of a size and shape to be grasped by the human hand;
   means for delivering said pulses into the interior of said handle;
   a nozzle for delivering said pulses against the teeth and gums of the user;
   means for mounting said nozzle to said handle for receiving said pulses;
   a toothbrush for scrubbing said teeth and massaging said gums;
   means for mounting said toothbrush to said handle;
   means included within said handle for moving said toothbrush relative to said handle in response to said pulses;

a valve disposed within said handle and actuatable automatically upon mounting of said nozzle to said handle for conveying said pulses only into said nozzle, said valve being actuated by the inner end of said nozzle upon its insertion into said handle;

and said valve being located within said handle in a position to be biased into its closed position by said pulses when so moving said toothbrush.

2. Apparatus as defined in claim 1 which further includes:

a manually-operable valve located in the path of said liquid received from said delivery means;

and means included in said path for accumulating pressure in said pulses when said valve is closed.

* * * * *